US00PP10216P

United States Patent [19]

Pieters

[11] Patent Number: Plant 10,216

[45] Date of Patent: Jan. 27, 1998

[54] CHRYSANTHEMUM PLANT NAMED 'ALDO'

[76] Inventor: Dirk Pieters, Schierveldestraat 3A, Oosnieuwkerke, 8840 Staden, Belgium

[21] Appl. No.: 754,942

[22] Filed: Nov. 25, 1996

[51] Int. Cl.[6] ..... A01H 5/00

[52] U.S. Cl. ..... Plt./79

[58] Field of Search ..... Plt./82.3, 74.1, Plt./76, 79

*Primary Examiner*—Howard J. Locker

*Attorney, Agent, or Firm*—C. A. Whealy

[57] ABSTRACT

A distinct cultivar of Chrysanthemum plant named 'Aldo', characterized by its upright, mounded and freely branching growth habit; moderate vigor; decorative-type inflorescences; bronze-colored ray florets; numerous inflorescences per plant; and good garden performance.

2 Drawing Sheets

1

The present invention relates to a new and distinct cultivar of garden Chrysanthemum plant, botanically known as *Dendranthema grandiflora* and referred to by the cultivar name Aldo.

The new cultivar is a product of a planned breeding program conducted by the inventor in Staden, Belgium. The objective of the breeding program was to create new garden Chrysanthemum cultivars that are freely branching and have numerous and long-lasting inflorescences.

The new cultivar originated from a cross made by the inventor of the nonpatented cultivar Red Emily as the female, or seed, parent with the nonpatented cultivar Draga as the male, or pollen, parent.

The new Chrysanthemum was discovered and selected by the inventor as a flowering plant within the progeny of the stated cross in a controlled environment in Staden, Belgium.

Asexual reproduction of the new cultivar by terminal cuttings taken at Staden, Belgium, has shown that the unique features of this new Chrysanthemum are stable and reproduced true to type in successive generations.

The following traits have been repeatedly observed and are determined to be the unique characteristics of 'Aldo'. These characteristics in combination distinguish 'Aldo' as a new and distinct cultivar:

1. Upright, mounded and freely branching growth habit, moderately vigorous.
2. Decorative-type inflorescences.
3. Bronze-colored ray florets.
4. Numerous inflorescences per plant.
5. Good garden performance.

The cultivar Aldo has not been observed under all possible environmental conditions. The phenotype may vary somewhat with variations in environment such as temperature, daylength and light intensity, without, however, any variance in genotype.

In side-by-side comparison in Staden, Belgium, under commercial practice, plants of the new Chrysanthemum differ from plants of the female parent, the cultivar Red Emily in ray floret color and inflorescence form. In the same comparisons, plants of the new Chrysanthemum differ from the male parent, the cultivar Draga, in ray floret color, foliage color and vigor.

Plants of the new Chrysanthemum can be compared to the cultivar Ginger (U.S. Plant Pat. No. 6,403). However, in side-by-side comparisons conducted in Oxnard, Calif., under commercial practice, plants of the new Chrysanthemum had darker ray floret color, darker foliage color, more inflorescences per plant, and flowered later than plants of the cultivar Ginger.

Plants of the new Chrysanthemum can also be compared to the cultivar Harvest Emily (U.S. Plant Pat. No. 9,075).

2

However, in side-by-side comparisons conducted in Oxnard, Calif., under commercial practice, plants of the new Chrysanthemum had smaller inflorescences and flowered later than plants of the cultivar Harvest Emily.

The accompanying colored photographs illustrate the overall appearance of the new cultivar, showing the colors as true as it is reasonably possible to obtain in colored reproductions of this type.

The first photograph comprises a side perspective view of a typical flowering 16.5-cm container of 'Aldo' with five cuttings in the container.

The second photograph comprises a close-up view of typical inflorescences of the new Chrysanthemum. Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with night temperatures ranging between 14 and 20C, day temperatures ranging between 20 and 30C, and average light levels of 5,000 to 6,000 footcandles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultivar Aldo.

Commercial classification: Garden chrysanthemum.

Parentage:

*Female, or seed, parent.*—*Dendranthema grandiflora* cultivar Red Emily (not patented).

*Male, or pollen, parent.*—*Dendranthema grandiflora* cultivar Draga (not patented).

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Upright with rounded inflorescence display. Moderate vigor and freely branching.

*Plant height.*—About 25 cm.

*Lateral branch length.*—About 20 to 22 cm.

*Quantity of lateral branches after removal of apical meristem.*—About 4 to 5.

*Stem color.*—138B.

*Foliage description.*—Number of leaves per plant: About 80 to 110. Number of leaves per lateral branch: About 20 to 22. Leaf arrangement: Alternate. Leaf size, fully expanded: Length: About 5 to 6.5 cm. Width: About 3 to 4 cm. Leaf apex: Mucronate. Leaf base: Attenuate. Leaf margin: Palmately lobed. Leaf texture: Abaxial and adaxial surfaces slightly pubescent, smooth and dull. Veins prominent on abaxial surface. Petiole length: About 2 to 2.5 cm. Color: Young foliage adaxial surface: 137B. Young foliage abaxial surface: 138B. Fully expanded foliage adaxial surface: 137B. Fully expanded foliage abaxial surface: 137C. Venation abaxial surface: 138B. Venation adaxial surface: 138B. Petiole: 138B.

Inflorescence description:

*Appearance.*—Decorative-type inflorescence form. Inflorescences borne on terminals above foliage, arising from leaf axils. Disc and ray florets arranged acropetally on a flat capitulum.

*Flowering response.*—Under natural conditions, plants flower in the autumn. Inflorescence initiation and development can be induced under short day/long night conditions (at least 13.5 hours of darkness). Plants exposed to 3 to 4 weeks of long day/short night conditions after sticking followed by photoconductive short day/long night conditions, flower about 56 days later. Inflorescences maintain good substance for 3 to 4 weeks under bright natural daylight.

*Quantity of inflorescences.*—About 10 to 15 inflorescences per flowering stem.

*Inflorescence size.*—Diameter: About 4.5 to 5 cm. Depth (height): About 1.5 to 2 cm. Diameter of disc: About 5 mm.

*Opening inflorescences.*—Bud shape: Spherical. Bud size: Length: About 1 cm. Width: About 1 cm. Bud color: 22A to 20A.

*Ray florets.*—Shape: Spatulate, elongated. Size: Length: About 2.5 cm. Width: About 5 to 7.5 mm. Apex: Obtuse/mucronate. Base: Attenuate. Margin: Entire. Texture: Velvety, soft, smooth and glabrous. Number of ray florets per inflorescence: About 75. Color: Multi-colored ranging from yellow to red-bronze. When opening, adaxial surface: 44A. When opening, abaxial surface: 8A. Mature, adaxial surface: 26A. Mature, abaxial surface: 8B. Fading to, adaxial surface: 9A/35B. Fading to, abaxial surface: 8B/8C. After senescence: 9B/26B/35B.

*Disc florets.*—Shape: Tubular, fluted at apex. Size: Length: About 5 mm. Width: About 1 mm. Number of disc florets per inflorescence: About 25 to 30. Color: Immature: 1A. Mature: 15A.

*Peduncle.*—Aspect: Rigid, erect. Length: First peduncle: About 3 to 3.5 cm. Fourth peduncle: About 3 to 4.5 cm. Texture: Pubescent: Color: 138B.

*Sepals.*—Shape: Linear. Apex: Acute. Margin: Entire. Texture: Fleshy. Quantity: About 50 to 55. Color: Adaxial surface: 138B. Abaxial surface: 137B/138B.

*Reproductive organs.*—Androecium: Not observed. Gynoecium: Present on both ray and disc florets. Stigma color: 15A. Style length: About 3 to 4 mm. Style color: 155B.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Aldo', as illustrated and described.

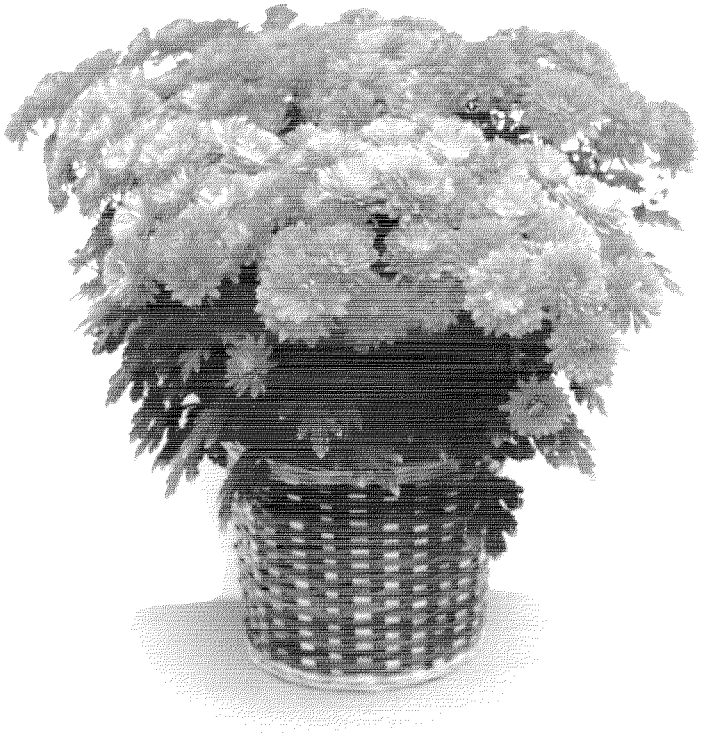

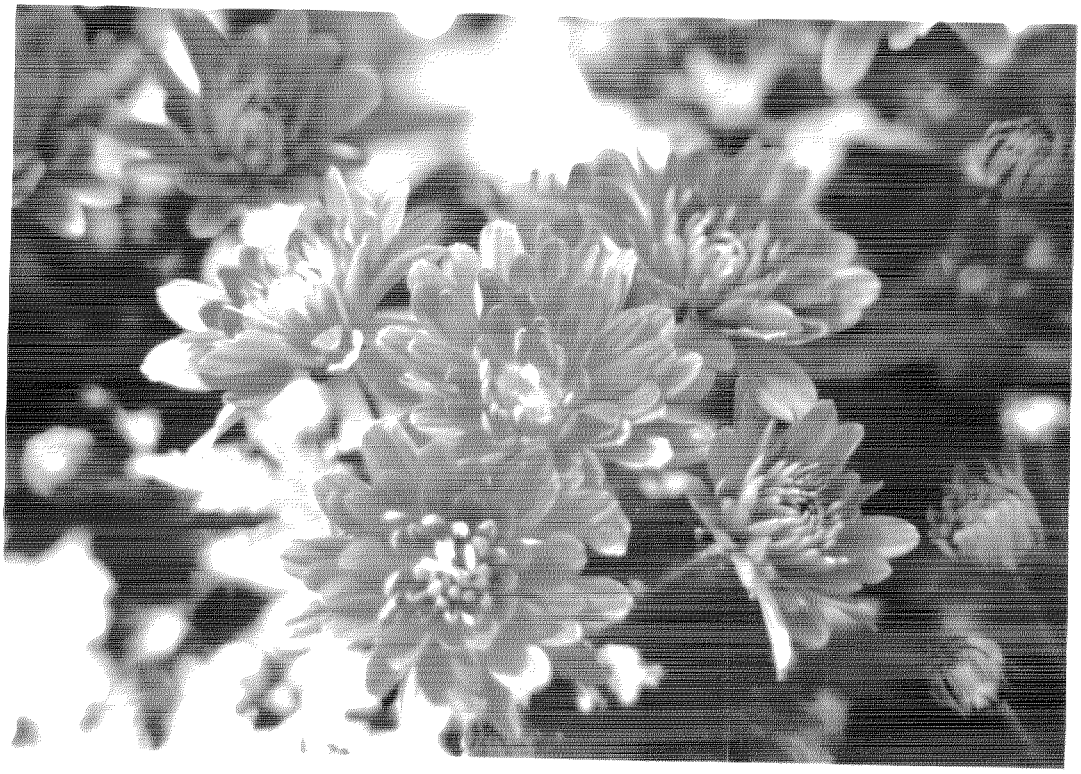

* * * * *